(12) United States Patent
Rucker

(10) Patent No.: US 7,727,270 B2
(45) Date of Patent: Jun. 1, 2010

(54) EXPANDABLE AND RETRIEVABLE STENT

(76) Inventor: Brian K. Rucker, 1148 Luke St., King, NC (US) 27021

( * ) Notice: Subject to any disclaimer, the term of this patent is extended or adjusted under 35 U.S.C. 154(b) by 1046 days.

(21) Appl. No.: 11/414,977

(22) Filed: May 1, 2006

(65) Prior Publication Data

US 2006/0259119 A1    Nov. 16, 2006

Related U.S. Application Data

(60) Provisional application No. 60/677,730, filed on May 4, 2005.

(51) Int. Cl.
A61F 2/06    (2006.01)
(52) U.S. Cl. ...................................... 623/1.11
(58) Field of Classification Search ................ 606/191, 606/112, 127, 198; 623/1, 17, 1.32, 1.33, 623/1.11–1.15, 23.7, 15, 13.16
See application file for complete search history.

(56) References Cited

U.S. PATENT DOCUMENTS

| | | | |
|---|---|---|---|
| 4,585,000 A * | 4/1986 | Hershenson | 606/194 |
| 4,675,361 A | 6/1987 | Ward, Jr. | |
| 4,762,128 A | 8/1988 | Rosenbluth | |
| 4,861,830 A | 8/1989 | Ward, Jr. | |
| 4,921,478 A * | 5/1990 | Solano et al. | 604/509 |
| 5,441,516 A | 8/1995 | Wang et al. | |
| 5,538,008 A | 7/1996 | Crowe | |
| 5,589,563 A | 12/1996 | Ward et al. | |
| 5,690,642 A | 11/1997 | Osborne et al. | |
| 5,814,061 A | 9/1998 | Osborne et al. | |
| 5,855,565 A | 1/1999 | Bar-Cohen et al. | |
| 6,156,062 A * | 12/2000 | McGuinness | 623/1.22 |
| 6,206,931 B1 | 3/2001 | Cook et al. | |
| 6,217,585 B1 * | 4/2001 | Houser et al. | 606/108 |
| 6,277,139 B1 * | 8/2001 | Levinson et al. | 606/200 |
| 6,371,961 B1 | 4/2002 | Osborne et al. | |
| 6,471,644 B1 * | 10/2002 | Sidor, Jr. | 600/204 |
| 6,692,497 B1 | 2/2004 | Tormala et al. | |
| 6,723,120 B2 * | 4/2004 | Yan | 623/1.15 |
| 6,752,826 B2 | 6/2004 | Holloway et al. | |
| 6,939,377 B2 | 9/2005 | Jayaraman et al. | |
| 7,572,273 B2 * | 8/2009 | Mazzocchi et al. | 606/200 |
| 2001/0053931 A1 * | 12/2001 | Hess et al. | 623/1.15 |

(Continued)

FOREIGN PATENT DOCUMENTS

CA    2 420 558 A1    8/2003

(Continued)

OTHER PUBLICATIONS

C. Heeschen et al., Nature Medicine 7 (2001), No. 7, 833-839.

(Continued)

*Primary Examiner*—Todd E Manahan
*Assistant Examiner*—Richard Dault

(57) ABSTRACT

An expandable and retrievable stent is disclosed herein. The stent includes an inner strut, a first traveling anchor movably attached to the inner strut and a second anchor secured to the inner strut. The stent further includes frame connected to the first traveling anchor and the second anchor wherein the frame has at least a radially compressed configuration and a radially expanded configuration. The stent may also include a generally cylindrical sleeve.

13 Claims, 11 Drawing Sheets

U.S. PATENT DOCUMENTS

| | | |
|---|---|---|
| 2002/0187288 A1 | 12/2002 | Lim et al. |
| 2003/0144670 A1 | 7/2003 | Pavcnik et al. |
| 2003/0149471 A1 | 8/2003 | Briana et al. |
| 2004/0073252 A1* | 4/2004 | Goldberg et al. ............ 606/200 |
| 2004/0225322 A1 | 11/2004 | Garrison et al. |
| 2005/0079199 A1 | 4/2005 | Heruth et al. |

FOREIGN PATENT DOCUMENTS

| | | |
|---|---|---|
| WO | WO 92/05829 A1 | 4/1992 |
| WO | WO 99/23976 A1 | 5/1999 |

OTHER PUBLICATIONS

C. Johnson et al., Circulation Research 94 (2004), No. 2, 262-268.

International Search Report dated Aug. 1, 2006 for International Application No. PCT/US2006/016524.

* cited by examiner

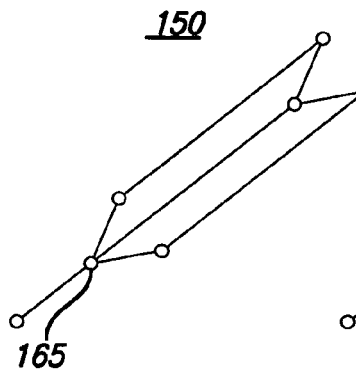
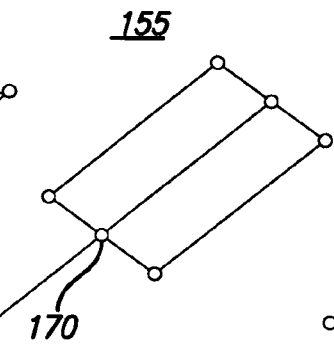
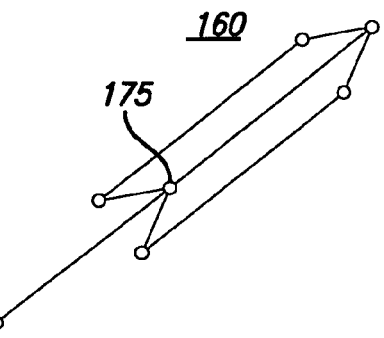
FIG. 4A     FIG. 4B     FIG. 4C
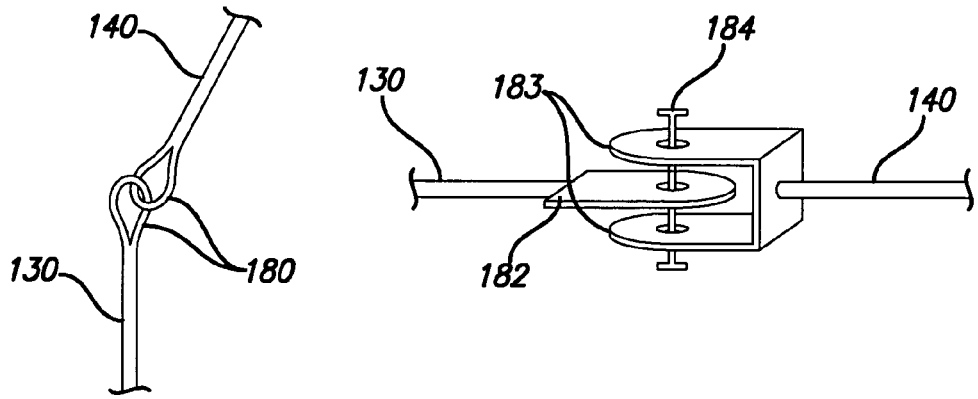
FIG. 5A     FIG. 5B
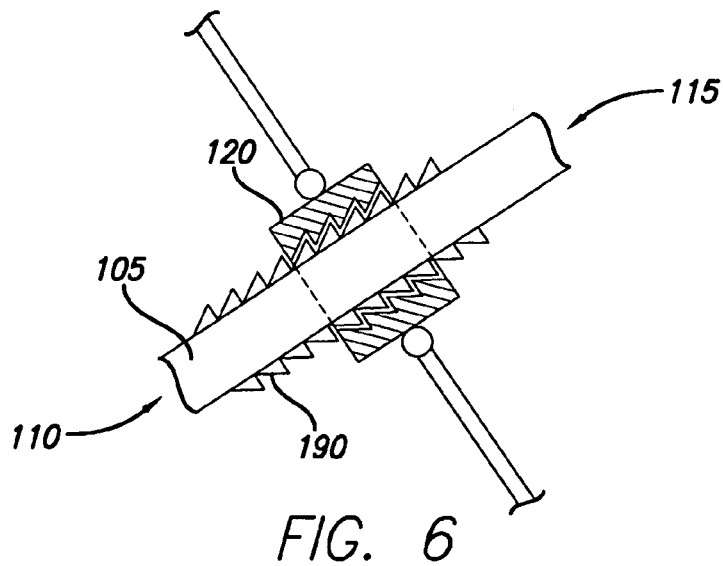
FIG. 6

EXPANDABLE AND RETRIEVABLE STENT

This application claims the benefit of U.S. Provisional Patent Application No. 60/677,730, filed May 4, 2005, which is incorporated by reference herein in its entirety.

BACKGROUND

A variety of body lumens are subject to undesired strictures or narrowing. For example, blood vessels can be blocked or narrowed by atherosclerosis, while esophageal strictures can arise from individual anatomical differences, or from diseases such as connective tissue disorders. Procedures for dilating or enlarging such strictures or narrowed regions often entail the use of a stent. The stent may be positioned across a particular stricture or narrowed region, and may then be expanded in order to widen the lumen without causing trauma to the wall of the lumen.

Unfortunately, the current stent designs may have a number of drawbacks. For instance, many types of stents cannot be retrieved once they have been deployed. This can be problematic, especially when the stent is no longer needed or when it malfunctions. Another shortcoming associated with many stent designs is that they undergo endothelialization, wherein the tissue of the dilated body lumen grows into the stent. Thus, even when a retrievable stent has been employed, it may not be possible to remove the stent without damaging the body lumen. Finally, many of the current stent designs cannot be compressed sufficiently for endoscope delivery (since the diameter of an endoscope delivery channel is somewhere around 4 mm).

An ideal stent would be highly compressible and thus amenable to endoscope delivery techniques, would be retrievable and may also discourage endothialization.

BRIEF SUMMARY

In one aspect of the invention, there is an expandable and retrievable stent comprising of an inner strut with an inner strut proximal end portion and an inner strut distal end portion. The stent also includes a distal anchor secured to the inner strut distal end portion, a plurality of distal arms attached to the distal anchor and a first traveling anchor movably attached to the inner strut. The first traveling anchor is located between the inner strut proximal end portion and the inner strut distal end portion. In addition, the stent has a plurality of proximal arms attached to the traveling anchor and a plurality of outer struts. Each of the outer struts extends between and is attached to one proximal arm at a proximal attachment and one distal arm at a distal attachment.

In another aspect of the present invention, an expandable and retrievable stent is provided. The stent includes an inner strut, a first traveling anchor movably attached the inner strut and a second anchor secured to the inner strut. The stent further includes a frame connected to the traveling anchor and the second anchor. The frame has at least a radially compressed configuration and a radially expanded configuration.

In another aspect of the present invention, an expandable and retrievable stent is provided. The stent includes an inner strut having a distal anchor and a first traveling anchor movably attached to the inner strut. A movable member is attached to the distal anchor and the first traveling anchor. The movable member has a radially compressed configuration and a radially expanded configuration. The stent may also include a sleeve connected to at least a portion of the movable member.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

FIGS. 4A, 4B, and 4C, respectively, illustrate a longitudinal view of an umbrella stent in a first compressed state, an expanded state and a second compressed state.

FIGS. 5A and 5B illustrate two pivoting attachment configurations.

FIG. 6 illustrates a longitudinal cross-sectional view of an inner strut and a traveling anchor, wherein the surface of the inner strut possesses sloping teeth and the traveling anchor acts as a pawl.

DETAILED DESCRIPTION OF THE DRAWINGS AND THE PRESENTLY PREFERRED EMBODIMENTS

An expandable and retrievable stent, which may also be referred to as an umbrella stent, is disclosed herein. This stent is designed such that it may be selectively converted between a first compressed state, an expanded state, and a second compressed state. This design may allow for delivery via a variety of low-profile devices, such as introduction via an endoscope delivery channel. In addition, the stent disclosed herein may be retrievable and may discourage endothelialization.

Figure 1:
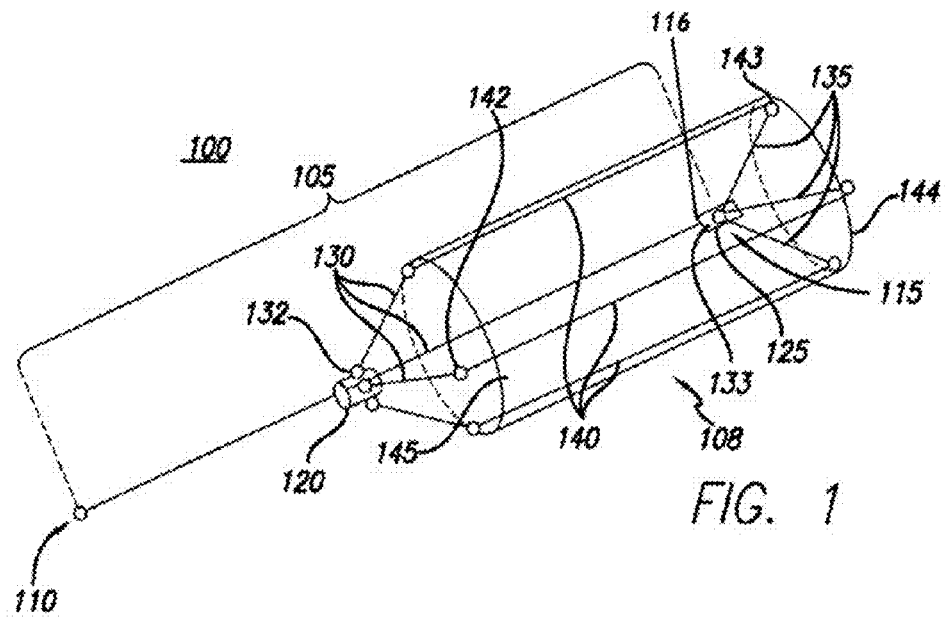
FIG. 1 illustrates a longitudinal view of an umbrella stent.

FIG. 1 illustrates a longitudinal view of an umbrella stent 100 having a movable member 108. The stent 100 may comprise an inner strut 105 that extends from an inner strut proximal end portion 110 to an inner strut distal end portion 115. A first traveling anchor 120 may be movably attached to the inner strut 105 and a distal anchor 125 may be attached to the inner strut distal end portion 115. In some embodiments, the distal anchor 125 may also be movable along the inner strut 105 with the endmost anchoring position being located at a distal end 116. The distal anchor 125 is secured to the inner strut 105 distal to the traveling anchor 120. The traveling anchor 120 may be operably attached to the movable member 108 that includes a plurality of proximal arms 130 by way of a plurality of inner proximal pivoting attachments 132. The distal anchor 125 may be pivotally attached to the movable member 108 that includes a plurality of distal arms 135 by way of a plurality of inner distal pivoting attachments 133. The movable member 108 may also include a plurality of outer struts 140, wherein each outer strut 140 may extend between and be pivotally attached to one proximal arm 130 and one distal arm 135. The attachment between the outer struts 140 and the proximal arms 130 may be formed by an outer proximal pivoting attachment 142. The attachments between the outer struts 140 and the distal arms 135 may be formed by an outer distal pivoting attachment 143. In one configuration, the stent 100 may include a generally cylindrical sleeve 144, sized and shaped to correspond to the lumen, which may be attached to the plurality of outer struts 140. The cylindrical sleeve 144, may extend along the entire length of the outer struts 140 or a portion thereof, thus defining a stent lumen 145. In one configuration, the cylindrical sleeve 144 may cover the outer proximal pivoting attachments 142 and the outer distal pivoting attachments 143. Covering the pivoting attachments 142 and 143 with the cylindrical sleeve 144 may prevent this endothelialization of the attachments 142 and 143. The length and thickness of the sleeve 144 will depend on the delivery site and the material(s) used to form the sleeve. In some embodiments, the thickness of the sleeve may be about 0.0001 to about 0.250 inches. Other thicknesses are also possible.

A variety of biocompatible materials may be employed to construct the stent 100, or portions of the stent 100, including a metal, a medically-acceptable polymer or a bioabsorbable polymer or material. The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The metal used for the stent or portions thereof may, among other things, comprise at least one of the following: stainless steel, tantalum, nitinol; gold, silver, tungsten, platinum, inconel, cobalt-chromium alloys and iridium, all of which are commercially available metals or alloys used in the fabrication of medical devices. In a preferred configuration, the stent 100 is constructed from nitinol, stainless steel and/or cobalt-chromium alloys.

The stent 100, or portions of the stent 100, may be constructed from any medically-acceptable polymer. For example, the polymer may be selected from the group consisting of cellulose acetate, cellulose nitrate, silicone, polyethylene, high density polyethylene, polyethylene teraphthalate, polyurethane, polytetrafluoroethylene, polyamide, polyester, polyorthoester, polyvinyl chloride (PVC), polypropylene, acrylonitrile-butadiene-styrene (ABS), polycarbonate, polyurethane, nylon silicone, and polyanhydride.

In one configuration, the stent 100 may be constructed from a combination of metals and polymeric materials.

The bioabsorbable polymer may, among other things, include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly (glycolic acid-cotrimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid.

One example of a bioabsorbable polymer is disclosed in U.S. Pat. No. 6,692,497, which is incorporated herein by reference. The bioabsorbable materials disclosed in U.S. Pat. No. 6,692,497 may be formed from a uni- and/or biaxially oriented bioabsorbable polymer, copolymer, polymer alloy or composite with particle filler or fiber reinforcement. An example of such a material is a lactide (80 mol %) and glycolide (20 mol %) copolymer composition which is oriented. Thus, in this configuration the stent 100, comprising a bioabsorbable material, will eventually dissolve and/or be absorbed. The rate at which bioabsorbable materials dissolve depends on such factors as chemical composition and molar mass of the bioabsorbable polymeric material, implant size and geometry or the position of the implant in the human body. Accordingly, the amount of time required to dissolve and/or be absorbed can be tailored to be fast or slow.

The cylindrical sleeve 144 may comprise a biocompatible polymer. Examples of biocompatible polymers include: polyesters, such as poly (ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; polyamides; and polyanhydrides.

The biocompatible polymer may further comprise a polyurethane, such as polyetherurethanes, polyurethane ureas, polyetherurethane ureas, polyurethanes containing carbonate linkages and polyurethanes containing siloxane segments.

The polyurethane also includes THORALON (THORATEC, Pleasanton, Calif.), which is a polyurethane base polymer blended with a siloxane containing surface modifying additive, as disclosed in U.S. Pat. Nos. 6,939,377 and 4,675,361, both of which are incorporated herein by reference in their entirety. THORALON is a polyurethane base polymer blended (referred to as BPS-215) with a siloxane containing surface modifying additive (referred to as SMA-300). The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates, pore forming agents or inorganic salts. Preferably the particulate is insoluble in the solvent. Examples of solvents include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can be substantially equal to the diameter of the salt grains.

The porous polymeric sheet can have a void-to-volume ratio from about 0.40 to about 0.90. Preferably the void-to-volume ratio is from about 0.65 to about 0.80. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. No. 6,752,826 and U.S. Patent Application Publication No. 2003/0149471 A1, both of which are incorporated herein by reference.

Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes may also be employed. These include polyurethane ureas that preferably include a soft segment and include a hard segment formed from a diisocyanate and diamine. For example, polyurethane ureas with soft segments such as polytetramethylene oxide, polyethylene oxide, polypropylene oxide, polycarbonate, polyolefin, polysiloxane (e.g. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

The diisocyanate used as a component of the hard segment may be represented by the formula OCN-R-NCO, where —R— may be aliphatic, aromatic, cycloaliphatic or a mixture of aliphatic and aromatic moieties. Examples of diisocyanates include tetramethylene diisocyanate, hexamethylene diisocyanate, 4,4'trimethyhexamethylene diisocyanate, tetramethylxylylene diisocyanate, -decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible polyurethanes modified with cationic, anionic and aliphatic side chains may also be used. See, for example, U.S. Pat. No. 5,017,664.

Other biocompatible polyurethanes include: segmented polyurethanes, such as BIOSPAN; polycarbonate urethanes, such as BIONATE; and polyetherurethanes such as ELAST-HANE; (all available from POLYMER TECHNOLOGY GROUP, Berkeley, Calif.).

Other biocompatible polyurethanes include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible polyurethanes may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

In addition, the cylindrical sleeve 144 may also comprise materials that are not inherently biocompatible, but that may be subjected to surface modifications in order to render the materials biocompatible. Examples of surface modifications include graft polymerization of biocompatiblepolymers from the material surface, coating of the surface with a crosslinked biocompatible polymer, chemical modification with biocompatible functional groups, and immobilization of a compatibilizing agent such as heparin or other substances. Thus, any polymer that may be formed into a sheet can be used to make the cylindrical sleeve 144, provided the final material is biocompatible.

In one configuration, the cylindrical sleeve 144 may be constructed from one of these biocompatible polymeric materials or a combination of these materials. In another configuration, the biocompatible polymeric material of the cylindrical sleeve 144 may be a film, for example a PTFE film or a Thoralon® film. In a further configuration, the biocompatible polymeric material of the cylindrical sleeve 144 may be a woven fabric, such as Dacron® (DUPONT, Wilmington, Del.). The sleeve 144 may also be made from a sheet or woven fabric of extracellular matrix material (ECM).

Connection of the cylindrical sleeve 144 to the movable member 108 may be by any method known to one of skill in the art. For example, the sleeve 144 may be adhered to the movable member 108 by physical or chemical means. In some embodiments, the sleeve 144 may be sewn to the movable member 108. Alternatively, the sleeve may be adhered to the movable member using a biocompatible adhesive similar to the adhesives listed below that may be used for adhering the stent 100 to the vessel wall. The connection between the sleeve 144 and the movable member 108 may also be bioresorbable, for example, allowing the movable member 108 to be easily removed after an appropriate period of time, leaving the sleeve 144 in the vessel or when the connection and the sleeve 144 are bioresorbable.

In some embodiments, for example, when a PTFE film or a Thoralon® film is used to form the sleeve 144, the sleeve 144 may be adhered to the movable member 108 as the sleeve 144 is formed, for example, by coating or spraying the Thoralon® onto a mandrel having the movable member 108 mounted on the mandrel. The Thoralon® may be coated onto the movable member 108 when the movable member is in the expanded configuration. The mandrel may then be removed and the movable member 108 and the sleeve 144 may be readily compressible for delivery to the vessel site. In some embodiments, where ECM is used to form at least a portion of the sleeve 144, the ECM may be added to the movable member 108 on a mandrel. The ECM may also be formed as a separate sheet used to form the sleeve 144 that may be sewn or adhered to the movable member 108. Any method used to attach the sleeve 144 to the movable member 108 may be used that will allow the sleeve 144 to move between the expanded configuration and the compressed configuration.

When included, the ECM may possesses biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

In one configuration, the cylindrical sleeve 144 may include a biologically active compound. The biologically active compound (e.g., pharmaceuticals) may include virtually any therapeutic substance that possesses desirable therapeutic characteristics for application to the implant site. These agents include: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, and gene therapy agents. The biologically active compound may be dispersed within the cylindrical sleeve 144 or may be applied to the surface of the cylindrical sleeve 144.

The dimensions of the various components of the stent 100 may be varied based on the desired use. In one configuration, the length of the inner strut 105 and the outer struts 140 may be altered based on the length of the stricture that is to be treated. In another configuration, the length of the proximal arms 130 and the distal arms 135 may be altered based on the diameter of the stricture that is to be treated. Moreover, it may be necessary to increase or decrease the diameter of the inner strut 105, the proximal arms 130, the distal arms 135, and/or the outer struts 140. For example, when a greater radial force is required to support a given stricture, it may be necessary to increase the diameter of the inner strut 105, the proximal arms 130, the distal arms 135, and/or the outer struts 140. In addition, the inner strut 105, the proximal arms 130, the distal arms 135, and/or the outer struts 140 may be curved or straight. Although FIG. 1 illustrates the stent 100 in a configuration having three proximal arms 130, three distal arms 135 and three outer struts 140, the number of proximal arms 130, distal arms. 135 and outer struts 140 may vary. For example, the stent 100 may have five proximal arms 130, five distal arms 135 and five outer struts 140.

Figure 2:
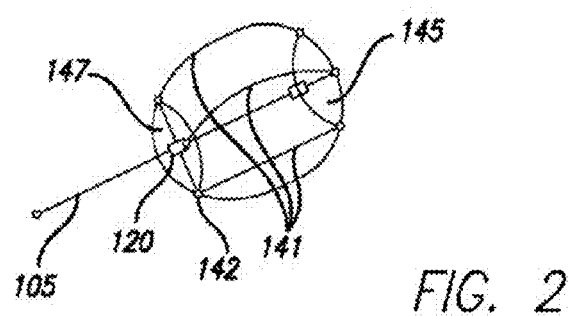
FIG. 2 illustrates an umbrella stent with a plurality of convex outer struts.

FIG. 2 illustrates a longitudinal view of an umbrella stent 100 with a plurality of convex outer struts 141. In one configuration, it may be desirable to employ convex outer struts 141, such that the convex outer struts 141 are concave in relation to the inner strut 105. Convex outer struts 141 may provide more efficient expansion of the cylindrical sleeve 144 and may create a tighter seal between the cylindrical sleeve 144 and the stricture in which the stent 100 is deployed. This may in turn ensure that any liquid traveling through the body lumen will pass through the stent lumen 145.

Figure 3:
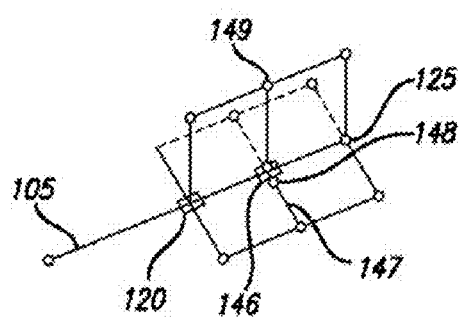
FIG. 3 illustrates an umbrella stent with a second traveling anchor and a plurality of central arms.

FIG. 3 illustrates a longitudinal view of the umbrella stent 100 with a second traveling anchor 146 and a plurality of central arms 147. In this configuration, the traveling anchor 146 may be movably attached to the inner strut 105 and may be positioned distal to the first traveling anchor 120 and proximal to the distal anchor 125. In addition, the plurality of central arms 147 may be attached to the second traveling anchor 146 by way of a plurality of inner central pivoting attachments 148. Each of the central arms 147 may also be attached to one of the outer struts 140 by way of an outer central pivoting attachment 149. In some instances it may be desirable to utilize the stent 100 in combination with the second traveling anchor 146, the central arms 147 and the pivoting attachments 148 and 149, since this arrangement may provide added support to the stricture in which the stent 100 is deployed.

FIGS. 4A, 4B and 4C, respectively, illustrate a longitudinal view of the umbrella stent 100 in a first radially compressed state 150, a radially expanded state 155 and a second radially compressed state 160, respectively. For purposes of simplicity, the umbrella stent 100 in FIGS. 4A, 4B and 4C has been depicted with only two proximal arms 130, two distal arms 135 and two outer struts 140. As will be understood by one skilled in the art, additional proximal arms, distal arms and outer struts are possible. In the first compressed state 150, the proximal arms 130 may be pivoted distally away from the traveling anchor 120 and the distal arms 135 may be pivoted distally away from the distal anchor 125. In one configuration of the first compressed state 150, the proximal arms 130 and the distal arms 135 may be substantially parallel with the inner strut 105, wherein substantially parallel refers to an angle of about 0° to about 20° between the inner strut 105 and the arms 130 and 135. In addition, while in the first compressed state 150, the traveling anchor 120 may be in a first position 165 and the cylindrical sleeve 144 may be folded, in a manner not shown in the Drawings, between each of the outer struts 140.

In the expanded state 155, the proximal arms 130 may be substantially perpendicular to the inner strut 105, wherein substantially perpendicular refers to a range of about 70° to about 110° in relation to the inner strut 105. In addition, while in the expanded state 155, the traveling anchor 120 may be in a second position 170.

In the second compressed state 160 the proximal arms 130 may be pivoted proximally away from the traveling anchor 120 and the distal arms 135 may be pivoted proximally away from the distal anchor 125. In one configuration of the second compressed state 150, the proximal arms 130 and the distal arms 135 may be substantially parallel with the inner strut 105, wherein substantially parallel refers to an angle of about 0° to about 20° between the inner strut 105 and the arms 130 and 135. In addition, while in the second compressed state 160, the traveling anchor 120 may be in a third position 175. Furthermore, the second compressed state 160 may be converted back to the expanded state 155.

In one configuration, the stent 100 may be selectively converted from the first compressed state 150 to the expanded state 155 and from the expanded state 155 to the second compressed state 160 by moving the traveling anchor 120 along the strut 105, such that the traveling anchor 120 is slid from the first position 165 to the second position 170 to the third position 175, respectively. As a result, the first position 165 may be proximal to the second position 170 and the second position may be proximal to the third position 175. Movement of the traveling anchor 120 along the strut 105 may thus concomitantly affect the position of the proximal arms 130 and distal arms 135, such that the stent 100 expands and collapses. The stent 100 may also be converted from the second compressed state 160 to the expanded state 155 and from the expanded state 155 to the compressed state 150.

The stent 100 may be deployed in either the first compressed state 150 or the second compressed state 160 and then converted to the expanded state 155. For example, in one configuration the stent 100 may be introduced in the second compressed state 160, converted to the expanded state 155 and retrieved after conversion back to the second compressed state 160. In a further configuration, the stent 100 may be introduced in the first compressed state 150, converted to the expanded state 155 and retrieved after conversion to the second compressed state 160. In another configuration, the stent 100 may be introduced in the first compressed state 150, converted to the expanded state 155 and retrieved after conversion back to the first compressed state 150. With regard to retrieval of the stent 100, the expanded state 155 may be converted to either the first compressed state 150 or the second compressed state 160, depending on the mechanism employed by the traveling anchor 120.

FIGS. 5A and 5B illustrate two pivoting attachment configurations. A variety of mechanisms may be employed to provide the pivoting attachments 132, 133, 142, 143, 148 and 149. In one configuration, the pivoting attachments 132, 133, 142, 143, 148 and 149 may consist of eyelets 180. For example, one of the outer proximal pivoting attachments 142 may be formed by looping together two eyelets 180, where one of the eyelets 180 is located on one of the proximal arms 130 and one of the eyelets 180 is located on one of the outer struts 140 as shown in FIG. 5A. In another configuration shown in FIG. 5B, the pivoting attachments 132, 133, 142, 143, 148 and 149 may be formed from a tongue 182, a groove 183 and a pin 184, where the tongue 182 fits into the groove 183 and the two are held together with the pin 184. Thus for example, the tongue 182 may be attached to one of the proximal arms 130, the groove may be attached to one of the outer struts 140 and the two may be held together by the pin 184, to provide one of the outer proximal pivoting attachments 142.

FIG. 6 illustrates a longitudinal cross-sectional view of the inner strut 105 and the first traveling anchor 120, wherein the surface of the inner strut 105 possesses sloping teeth 190 and the traveling anchor 120 acts as a pawl. Once the stent has been converted to the expanded state 155 from either the first compressed state 150 or the second compressed state 160, continued support within the stricture requires that the traveling anchor 120 remain substantially in the second position 170. If the traveling anchor 120 moves substantially towards the first position 165 or the third position 175, the overall diameter of the stent 100 may decrease and the stent lumen 145 may partially collapse. A decrease in the diameter of the stent 100 may also eliminate some or all of the support that is being provided to the stricture in which the stent 100 has been deployed.

In one configuration, a ratchet mechanism may be employed to ensure that the stent 100 will not collapse due to movement of the traveling anchor 120. The sloping teeth 190 may be oriented such that the traveling anchor 120 can only travel distally, thus preventing reversion of the stent 100 back to the first compressed state 150. Moreover, the size and angle of the sloping teeth 190 should be designed to ensure that the traveling anchor 120 will not travel distally (toward the third position 175) without additional manipulation by the physician, thus preventing conversion of the stent 100 to the second collapsed state 160. Thus, in this configuration, the stent 100 would be inserted in the first compressed state 150 and retrieved in the second compressed state 160. Manipulation of the traveling anchor 120, employing a ratchet mechanism, may be achieved as illustrated in FIGS. 1A-1D or FIGS. 13A-13F depending on the orientation of the sloping teeth 190.

Figure 7:
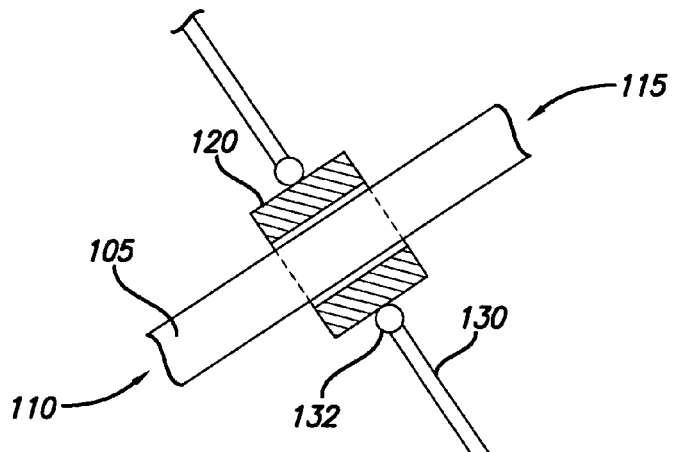
FIG. 7 illustrates a longitudinal cross-sectional view of an inner strut and a first traveling anchor, wherein a friction fit exists between the traveling anchor and the inner strut.

FIG. 7 illustrates a longitudinal cross-sectional view of the inner strut 105 and the first traveling anchor 120, wherein a friction fit exists between the traveling anchor 120 and the inner strut 105. The friction fit as described herein, provides another method of ensuring that the expanded state 155 does not convert to the first compressed state 150 or to the second compressed state 160, without additional manipulation, i.e., without force being applied to the traveling anchor 120. The friction fit between the traveling anchor 120 and the inner strut 105 may be achieved by sizing the traveling anchor 120 and the inner strut such that the traveling anchor fits tightly over the inner strut 105. Thus, in this configuration, a certain amount of force must be applied to the traveling anchor 120 before it will slide along the inner strut. However, the friction fit should not be so tight that the traveling anchor 120 cannot be slid along the inner strut 105. Manipulation of the traveling anchor 120 should result in conversion of the stent 100 from the first compressed state 150 or the second compressed state 160 to the expanded state 155. In addition, the friction fit should also allow for manipulation of the expanded state 155, such that it can be converted to either the first compressed state 150 or the second compressed state 160, if retrieval is desired. Manipulation of the traveling anchor 120, wherein the traveling anchor 120 employs a friction fit, may be achieved as illustrated in FIGS. 11A-11D or FIGS. 13A-13F.

Figure 8A:
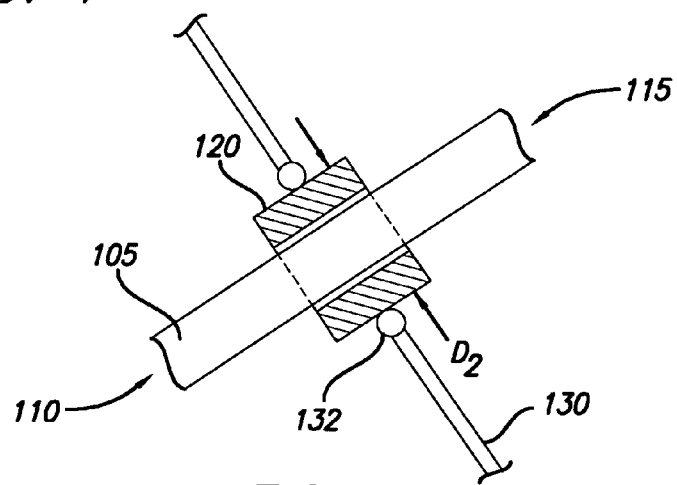
FIGS. 8A and 8B, respectively, illustrate a longitudinal cross-sectional view of a traveling anchor and its conversion from a reduced diameter $D_2$ to an expanded diameter $D_1$.
Figure 8B:
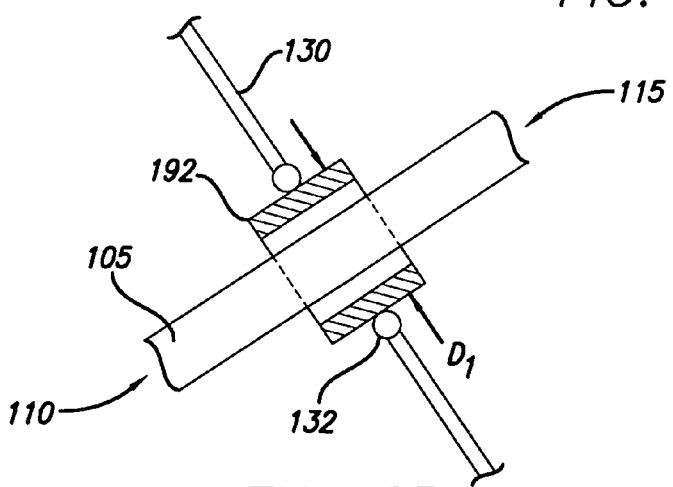

FIGS. 8A and 8B, respectively, illustrates a longitudinal cross-sectional view of the traveling anchor 120 and its conversion from a reduced diameter $D_2$ to an expanded diameter $D_1$. In this configuration, the traveling anchor 120 initially employs a friction fit as illustrated in FIG. 7. However, conversion of the stent 100 from the expanded state 155 to either the first compressed state 150 or the second compressed state 160 may be more easily achieved when the traveling anchor 120 comprises a shape memory material which can be converted from the reduced diameter $D_2$ to the expanded diameter $D_1$. In this configuration, the expanded diameter $D_1$, is greater than the reduced diameter $D_2$, which should eliminate the friction fit between the traveling anchor 120 and the inner strut 105. Thus, the traveling anchor 120 will possess a friction fit with the inner strut 105 during conversion of the stent 100 to the expanded state 155 and also while the stent 100 is in the expanded state 155. However, when retrieval of the stent 100 is desired, the traveling anchor 120 may be selectively converted from the reduced diameter $D_2$ to the expanded diameter $D_1$, thus eliminating the friction fit and allowing easier conversion from the expanded state 155 to the first compressed state 150 or the second compressed state 160.

Figure 12:
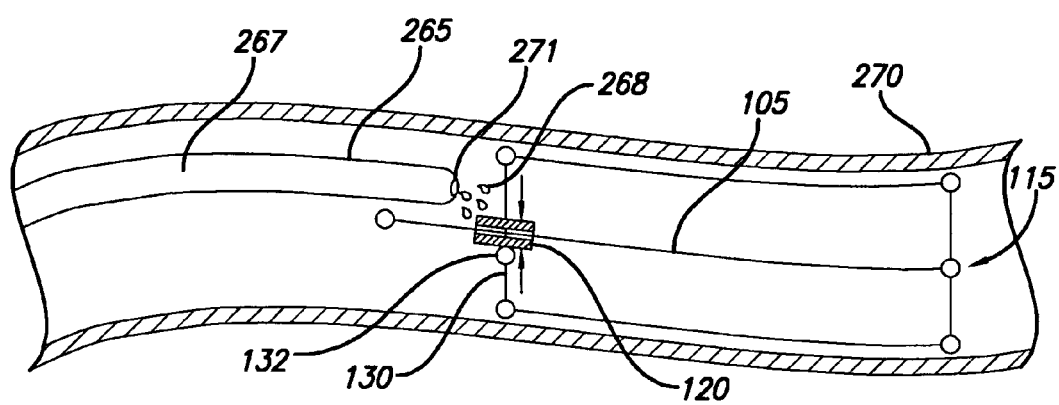
FIG. 12 illustrates a cross-sectional view of an umbrella stent and a temperature changing device.

In this configuration, conversion of the traveling anchor 120 from the reduced diameter $D_2$ to the expanded diameter $D_1$ may be achieved by increasing the temperature of the traveling anchor 120 to above the transition temperature of the shape memory alloy (See FIG. 12). The transition temperature of the traveling anchor 120 should be set above body temperature, but below a temperature that would harm tissues adjacent to the traveling anchor 120.

A variety of shape memory alloys may be employed, such as Ni—Ti binary alloy (nitinol alloy), Cu—Al—Ni ternary alloy, or Cu—Zn—Al ternary alloy. Preferably the traveling anchor 120 consists of a Ni—Ti binary alloy two-way shape memory alloy containing essentially about 51 atomic % of Ni and the balance substantially Ti. The traveling anchor 120, when using a shape memory material, may retain a superelasticity and therefore be capable of large elastic deformations. Additionally, the shape memory material is usually dependent on very small concentrations of elements other than nickel or titanium, e.g., a few parts per million of copper. The transition temperature is the temperature at which shape memory and is determined in one configuration by the amount of nitinol raw material that is in the traveling anchor 120.

In this configuration, as previously noted, the traveling anchor 120 retains the reduced diameter $D_2$ at temperatures below or at about the body temperature, i.e., at about 35° C. to about 37° C. Preferably, the transition temperature is above body temperature but below a temperature that would harm tissues adjacent to the traveling anchor 120, i.e., above about 35° C. and below about 100° C. More preferably, the transition temperature is above 37° C. and below about 75° C., and most preferably above about 40° C. and below about 60° C.

Figure 9A:
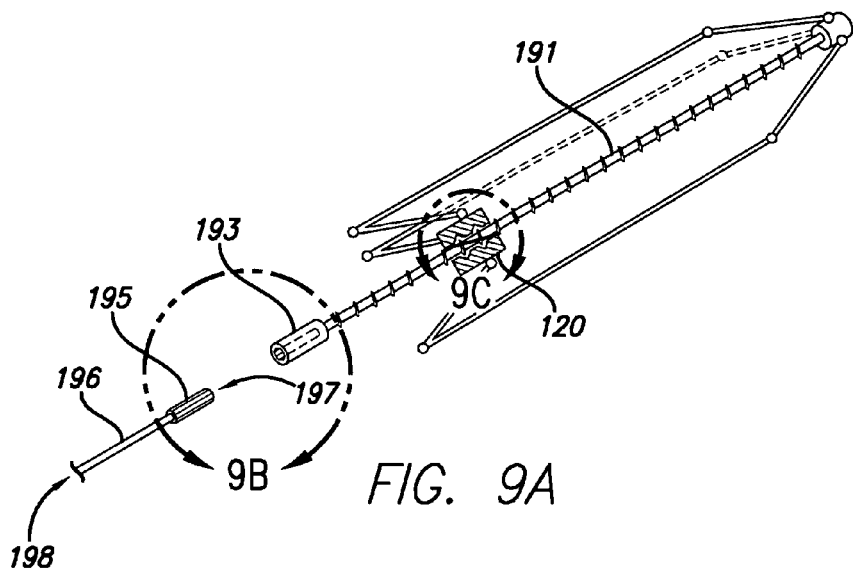
FIGS. 9A, 9B, and 9C illustrate an umbrella stent with a longitudinal cross-sectional view of a first traveling anchor and an inner strut, wherein the surface of the inner strut comprises a plurality of helical or spiral threads.
Figure 9B:
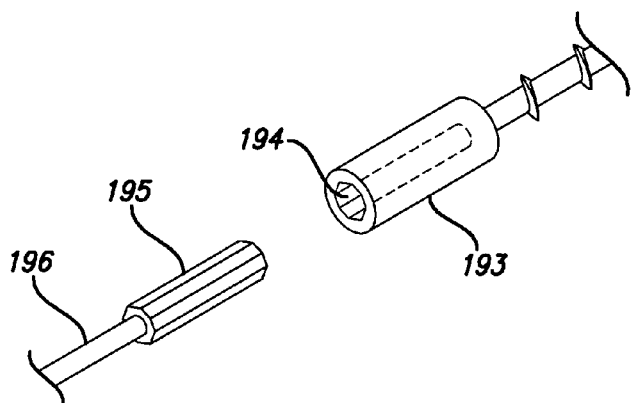
Figure 9C:
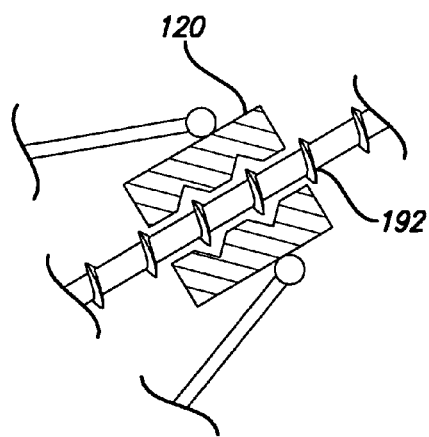

FIGS. 9A-9C illustrate the umbrella stent 100 with a longitudinal cross-sectional view of the first traveling anchor 120 and the inner strut 105, wherein the surface of the inner strut 105 comprises a plurality of helical or spiral threads 191. In this configuration, the inner surface of the traveling anchor 120 comprises grooves 192 corresponding to the spiral threads 191 (FIG. 9C). In addition, the distal anchor 125 is rotatably attached to the inner strut 105, thus allowing the inner strut 105 to be twisted or rotated.

In this configuration, twisting the inner strut 105 in relation to the traveling anchor 120 and the distal anchor 125 will cause the traveling anchor 120 to travel along the length of the inner strut 105. In one configuration, the threads 191 and the grooves 192 are constructed such that twisting of the inner strut 105 in a clockwise direction results in movement of the traveling anchor 120 toward the stent proximal end portion 110, while counterclockwise twisting of the inner strut 105 results in movement of the traveling anchor 120 toward the distal end portion 115. In another configuration, the threads 191 and the grooves 192 are constructed such that twisting of the inner strut 105 in a clockwise direction results in movement of the traveling anchor 120 toward the stent distal end portion 115, while counterclockwise twisting of the inner strut 105 results in movement of the traveling anchor 120 toward the proximal end portion 110.

Twisting the inner strut 105 may be carried out using a variety of manipulation apparatuses. In one configuration, the stent 100 may have a junction 193 attached to the proximal end portion 110, wherein the junction 193 defines a receiving port 194. As shown in FIG. 9B, the receiving port 194, which serves to receive a manipulation plug 195 that is attached to a distal end 197 of the manipulation device 196, may comprise a variety of shapes, such as an octagon, rectangle or square. However, the shape of the receiving port 194 must be selected such that when the manipulation plug 195 is inserted into the receiving port 194, twisting of the manipulation device 196 will translate into twisting of the inner strut 105. For example, the receiving port 194 may be an octagon space (as shown in FIG. 9C) that will accept an octagon shaped manipulation plug 195. The manipulation device 196 may comprise a wire or cannula that can be introduced into a patient to the site of the stent 100, wherein the manipulation device 196 extends between the distal end 197 and a proximal end 198. In one configuration, the proximal end 198 remains exterior to the patient such that it can be manipulated. The manipulation device 196 may be inserted via a variety of techniques. For example, the manipulation device 196 may be inserted via a catheter and/or endoscope (not shown).

The aspects of the stent 100 illustrated in FIGS. 4A-4C provide a method of converting the stent 100 from either of the collapsed states 150 or 160 to the expanded state 160. Furthermore, this configuration provides a method of converting the expanded state 155 to either of the collapsed states 150 or 160. However, conversion of the expanded state 160 to either of the collapsed states 150 or 160 should not occur without manipulation by the manipulation device 196.

Figure 10A:
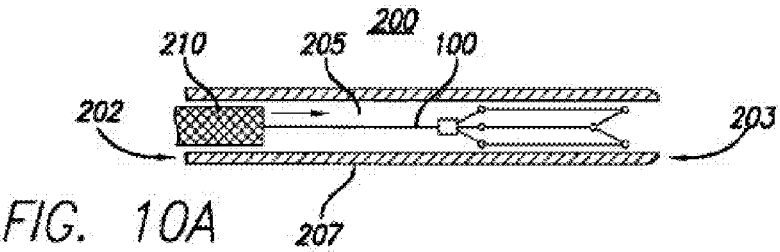
FIGS. 10A and 10B illustrate a longitudinal cross-sectional view of a delivery catheter in combination with an umbrella stent.
Figure 10B:
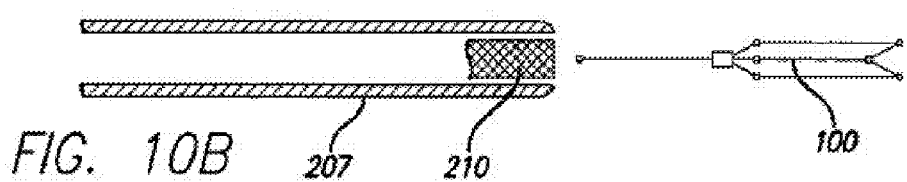

FIGS. 10A and 10B illustrate a longitudinal cross-sectional view of a delivery catheter 200 in combination with an umbrella stent 100. A variety of techniques may be employed to deliver the stent 100. In addition, delivery of the stent 100 and subsequent conversion of the stent 100 from the first compressed state 150 to the expanded state 155 may be carried out using a variety of techniques. For example, the stent 100 may be delivered with the delivery catheter 200 and may then be converted to the expanded state 155 using a second catheter. See FIGS. 1A-1D or FIGS. 13A-13F.

The delivery catheter 200 may extend between a proximal catheter end 202 and a distal catheter end 203. The delivery catheter 200 may include a lumen 205, defined by a catheter wall 207, as well as a pusher 210 that may be located within the lumen 205. The pusher 210 may be manipulated by a physician such that it may travel axially within the lumen 205. The stent 100, which is in the first compressed state 150, may be loaded into the distal catheter end 203 such that the stent 100 is distal to the pusher 210.

A number of techniques may be used to introduce the catheter 200 into a patient. For example, an endoscope may be inserted into a patient and the catheter 200 may be subsequently deployed via an endoscope channel (not shown). Once the catheter 200 reaches the desired position within a lumen, the stent 100 may be expelled with distal movement of the pusher 210, relative to the catheter wall 207. Exemplary deployment apparatuses are described in U.S. Patent Application Publication Nos. 2004/0225322 and 2003/0144670, which are herein incorporated by reference in their entirety. Alternatively, rapid exchange catheters may be used, such as a rapid exchange delivery balloon catheter which allows exchange from a balloon angioplasty catheter to a delivery catheter without the need to replace the angioplasty catheter wire guide with an exchange-length wire guide before exchanging the catheters. Exemplary rapid exchange catheters that may be used to deliver the valve device of the present invention are described in U.S. Pat. Nos. 5,690,642; 5,814,061; and 6,371,961 which are herein incorporated by reference in their entirety.

Figure 11A:
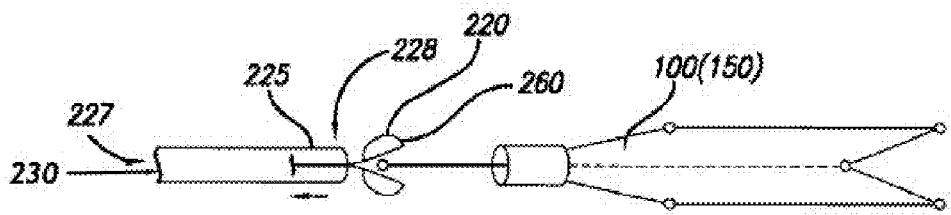
FIGS. 11A-11D illustrate manipulation forceps and a manipulation sheath in combination with an umbrella stent.
Figure 11B:
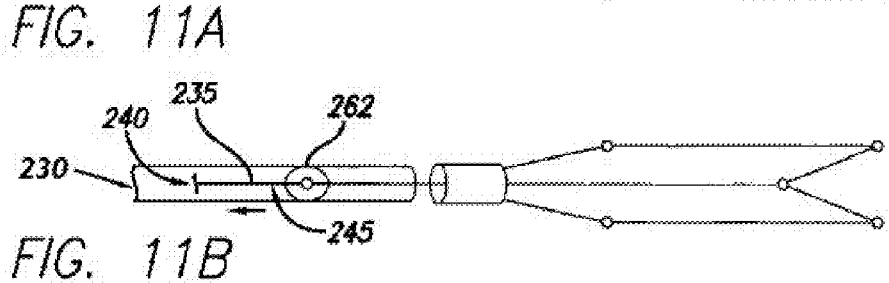
Figure 11C:
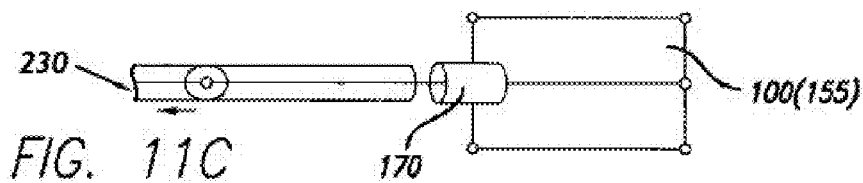

FIGS. 11A-11D illustrate manipulation forceps 220 and a manipulation sheath 225 in combination with the umbrella stent 100. A variety of techniques may be employed to convert the stent 100 from the first compressed state 150 to the expanded state 155, for example this may be achieved using manipulation forceps 220. Any type of forceps and stent manipulation device known to one of skill in the art may be used with the present invention. A specific example of manipulation forceps 220, as defined herein, is described in U.S. Pat. No. 5,538,008 issued to Crowe, which is incorporated herein by reference in its entirety. The manipulation sheath 225 extends between a manipulation sheath proximal end 227 and a manipulation sheath distal end 228. The manipulation sheath 225 may define a lumen 230, in which is located an inner cannula 235. The inner cannula 235 may extend between an inner cannula proximal end 240 and an inner cannula distal end 245, wherein the inner cannula distal end 245 may be integral with the delivery forceps 220. The forceps 220 are displaceable towards and away from one another and are formed from a resilient material. In addition, the forceps 220 are biased into a normally open configuration 260, which may be realized when the inner cannula distal end 245 is extended beyond the manipulation sheath distal end 228 (FIG. 11A). The forceps 220 may also have a closed configuration 262, which may be realized when the jaws 220 are withdrawn into the manipulation sheath 225 (FIG. 11B):

Conversion of the stent 100 from the first compressed state 150 to the expanded state 155 may be achieved by converting the forceps 220 from the open configuration 260 to the closed configuration 262, such that the closed configuration 262 encloses the inner strut proximal end portion 110 (FIG. 11B). Next the inner strut proximal end portion 110 may be pulled into the lumen 230 by withdrawing the forceps 220 proximally with respect to the manipulation sheath 225 (FIG. 11C). The manipulation sheath distal end 228 and the traveling anchor 120 may be sized such that the traveling anchor 120 is larger than the manipulation sheath distal end 228. Thus, as the stent 100 is pulled further into the lumen 230, the traveling anchor 120 will contact the manipulation sheath distal end 228 and further proximal movement of the forceps 220 will apply a force in the distal direction to the traveling anchor 120, causing the traveling anchor 120 to travel distally in relation to the inner strut distal end portion 115. As a result, the traveling anchor 120 may be converted from the first position 165 to the second position 170 and the stent will concomitantly be converted from the first compressed state 150 to the expanded state 155, which in turn will expand the cylindrical sleeve 144 to provide the stent lumen 145 (FIG. 11C).

Figure 11D:
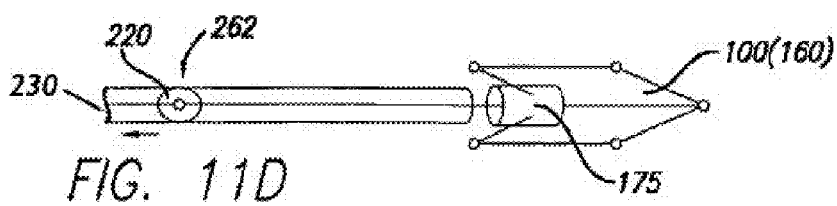

Conversion of the stent 100 from the expanded state 155 to the second compressed state 160 may employ a similar technique. However, in this case the force applied to the traveling anchor 120 results in conversion from the second position 170 to the third position 175 (FIG. 11D).

FIG. 12 illustrates a cross-sectional view of the umbrella stent 100 and a temperature changing device 265. As illustrated in FIGS. 8A and 8B, conversion of the traveling anchor 120 from the reduced diameter $D_2$ to the expanded diameter $D_1$ may be achieved by increasing the temperature of the traveling anchor 120 to above the transition temperature. This may be accomplished using a temperature changing device 265, which may be any device which can be used to change the temperature of the traveling anchor 120 to above the transition temperature, such as a heating apparatus, an electrical device, or a lumen which carries a hot liquid or gas. For example, when a heated liquid is used, the liquid may be any sterile liquid that is suitable for injecting into a patient and that is suitable for heating above the transition temperature described below. The suitable liquid may be saline, water and oils, with or without adjuvants, excipients or stabilizers when an additive may be included, such as anti-inflammatory compounds or antithrombogenic compounds. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol may be used provided the solution is stable upon heating to the transition temperature. Upon changing the temperature of the traveling anchor 120, the traveling anchor 120 expands to the expanded diameter $D_1$, as illustrated in FIG. 8B. Since the expanded diameter $D_1$, of the traveling anchor 120 is greater than the reduced diameter $D_2$, the stent 100 may be readily collapsed to either the first collapsed state 150 or the second collapsed state 160 (See FIGS. 11A-11D and 13A-13F.)

In one configuration, the temperature changing device 265 is a warming lumen 267. The warming lumen 267 carries a hot fluid 268 used to raise the temperature of the traveling anchor 120 above its transition temperature, but below a tissue harming temperature. Once the warming lumen 267 has been introduced into a vessel 270, the warming lumen 267 can be manipulated such that it dispenses the hot fluid 268 onto the traveling anchor 120 via a warming fluid port 271, thereby raising the temperature of the traveling anchor 120 above the transition temperature.

FIGS. 13A-F illustrate a longitudinal cross-sectional view of delivery forceps 220 and the manipulation sheath 225 in combination with the umbrella stent 100. In this configuration, the delivery forceps 220 and the manipulation sheath 225 are employed to collapse the stent 100, wherein the stent 100 employs the traveling anchor 120 having a friction fit to the inner strut 105.

Figure 13A:
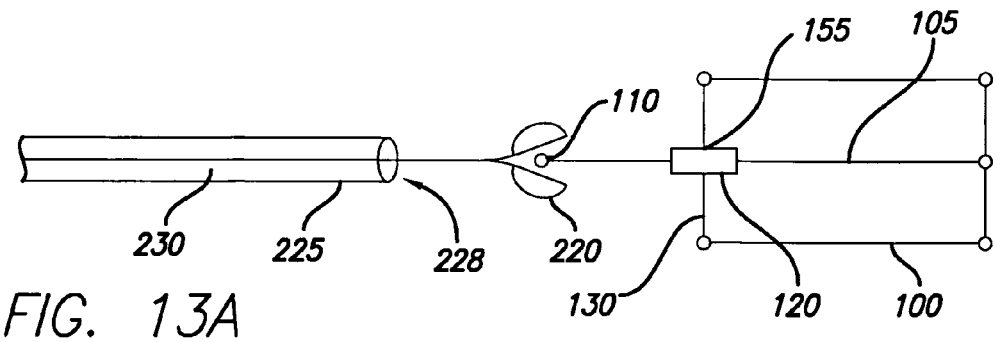
FIGS. 13A-13F illustrate a longitudinal cross-sectional view of delivery forceps and a manipulation sheath in combination with an umbrella stent.
Figure 13B:
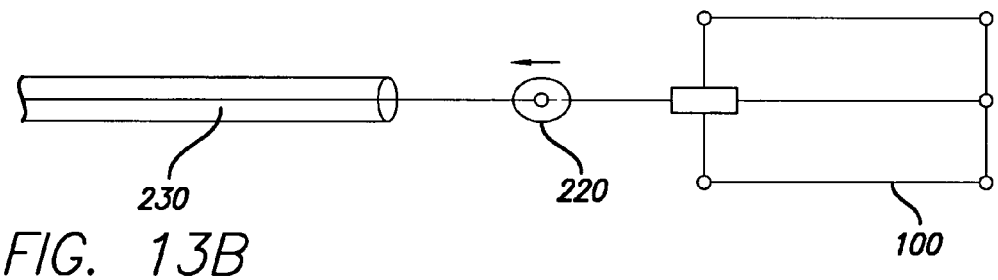
Figure 13C:
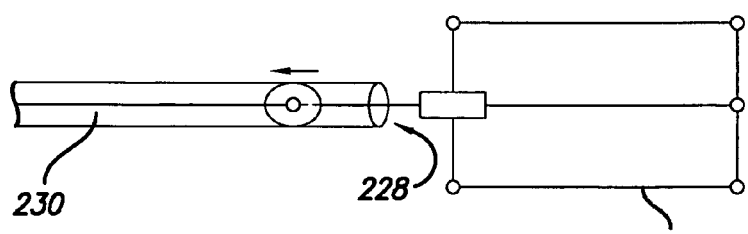
Figure 13D:
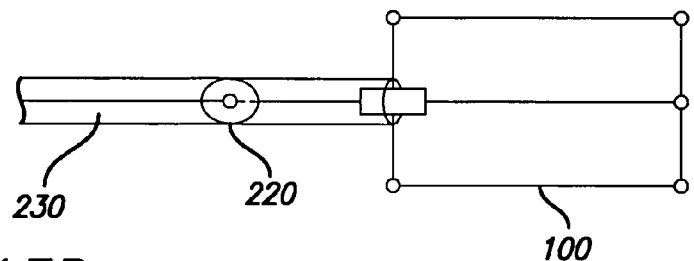
Figure 13E:
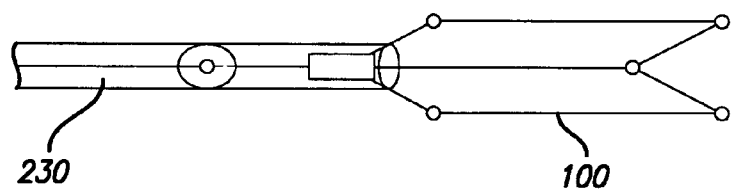
Figure 13F:
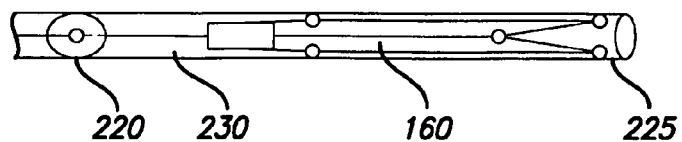

In this configuration, conversion of the stent 100 from the expanded state 155 to the second compressed state 160 is achieved by grasping the inner strut proximal end portion 110 with the forceps 220 (FIG. 13A). Next the inner strut proximal end portion 110 may be pulled into the lumen 230 by pulling the forceps 220 proximally in relation to the manipulation sheath distal end 228, i.e., further into the manipulation sheath 225, with respect to the manipulation sheath 225 (FIG. 13B). The manipulation sheath distal end 228 and the traveling anchor 120 may be sized such that the traveling anchor 120 will slide un-impeded into the lumen 230 (FIG. 13C). Thus, as the stent 100 is pulled further into the lumen 230, the proximal arms 130 will contact the manipulation sheath distal end 228 (FIG. 13D). Further proximal movement of the forceps 220 in relation to the manipulation sheath 225 will thus push the proximal arms 130 distally in relation to the inner strut 105, converting the stent 100 from the expanded state 155 to the second compressed state 160 while concomitantly pulling the stent 100 within the lumen 230 (FIG. 13E). Once the stent 100 is substantially within the lumen 230, the manipulation sheath 225 can be withdrawn from the patient (FIG. 13F).

Figure 14:
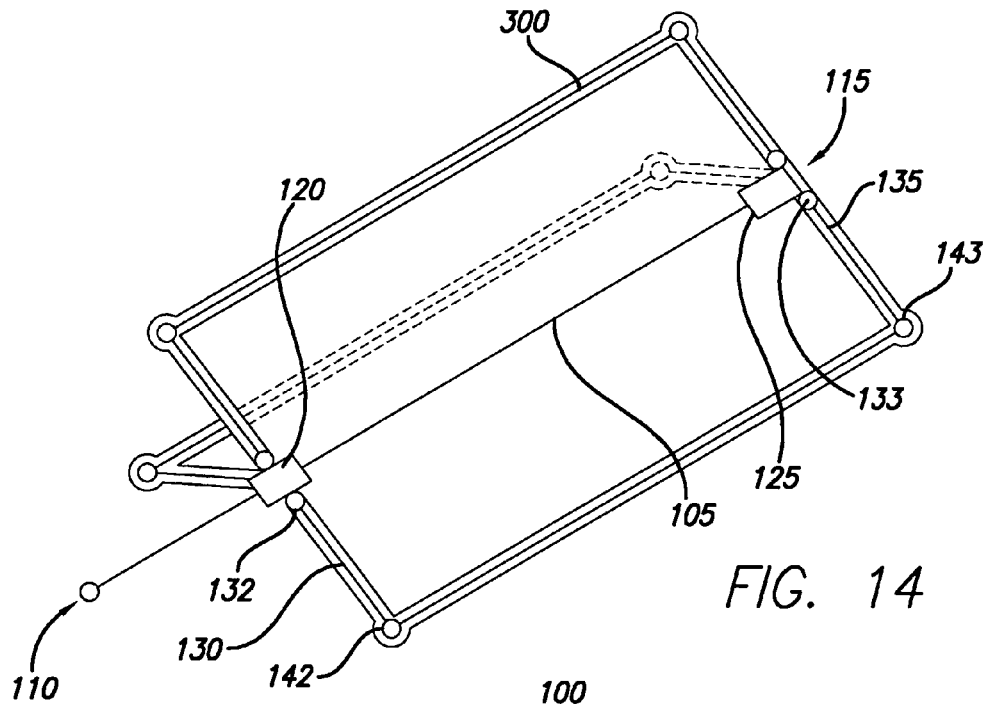
FIG. 14 illustrates an umbrella stent, wherein the stent possesses a coating, the coating being a biocompatible polymeric coating, a bioabsorbable polymer coating and/or a biologically active coating.

FIG. 14 illustrates the umbrella stent 100, wherein the stent 100 possesses a coating 300. The coating 300 may comprise a biocompatible polymer material or a bioabsorbable polymer material. The biocompatible polymer material and the bioabsorbable polymer material include those materials listed for the previously discussed biocompatible polymers and bioabsorbable polymers, respectively. The coating 300 may also comprise a biologically active material that is either employed alone or in combination with the biocompatible polymeric material and/or the bioabsorbable polymer material.

The coating 300 may further comprise carbohydrate materials such as carboxymethylcellulose, methylcellulose, agar, dextran, dextrin, carrageenan, xanthan, and guar.

The biologically active material (e.g., pharmaceuticals) may include virtually any therapeutic substance that possesses desirable therapeutic characteristics for application to the implant site. These agents include: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, and gene therapy agents.

The coating 300 may be selectively applied to different areas of the stent 100. For example, the coating 300 maybe applied selectively to the outer struts 140. In one configuration, the coating 300 may be selectively applied to the inner and/or outer surface of the outer struts 140. In a further configuration, different coatings 300 may be applied to the inner surface and the outer surface of the outer struts 140. In another configuration, the coating 300 may be applied selectively to the outer pivoting attachments 142 and 143.

In one configuration, the coating 300 may comprise the biologically active material without any biocompatible polymeric material or bioabsorbable polymer material. In another configuration, the coating 300 may comprise the biocompatible polymeric material or the bioabsorbable polymer material in combination with the biologically active material, such that the biocompatible polymeric material or the bioabsorbable polymer material is capable of releasing the biologically active material into the body at a predetermined time and at a predetermined rate. For example, the biologically active material may be dispersed within the biocompatible polymeric material or may be applied to the surface of the biocompatible polymeric material. In a further configuration, the coating 300 may comprise the biocompatible material coating applied over the biologically active material. In another configuration, the bioabsorbable polymer material may be applied over the biologically active material. In an additional configuration, a plurality of biologically active materials may be applied simultaneously.

Figure 15A:
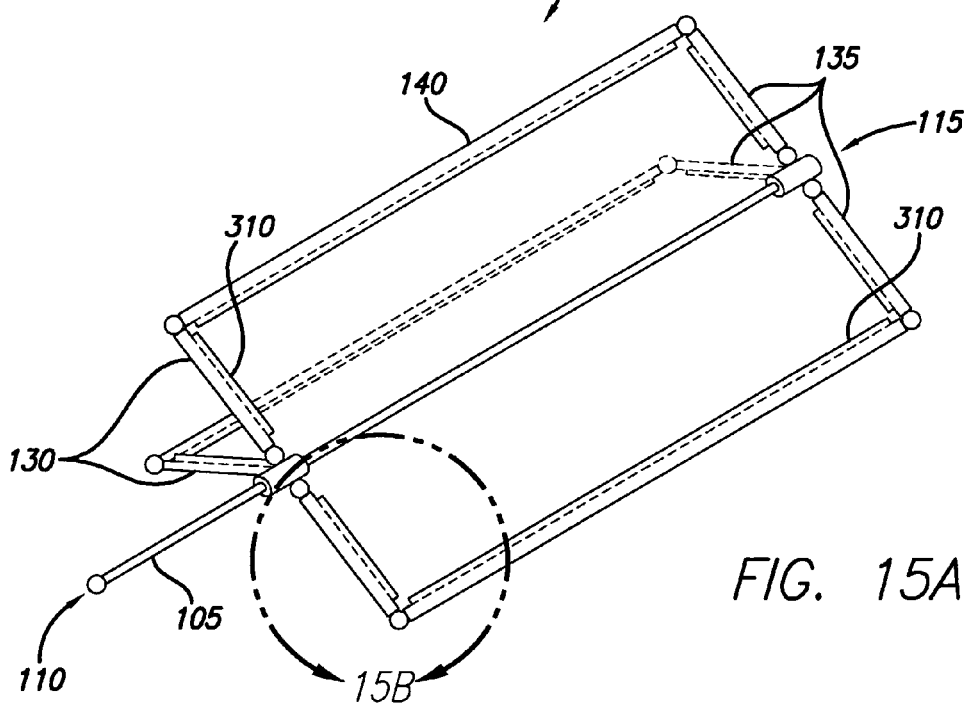
FIGS. 15A and 15B illustrate a longitudinal view of an umbrella stent, wherein portions of the proximal arms, distal arms and outer struts include a sharp edge.
Figure 15B:
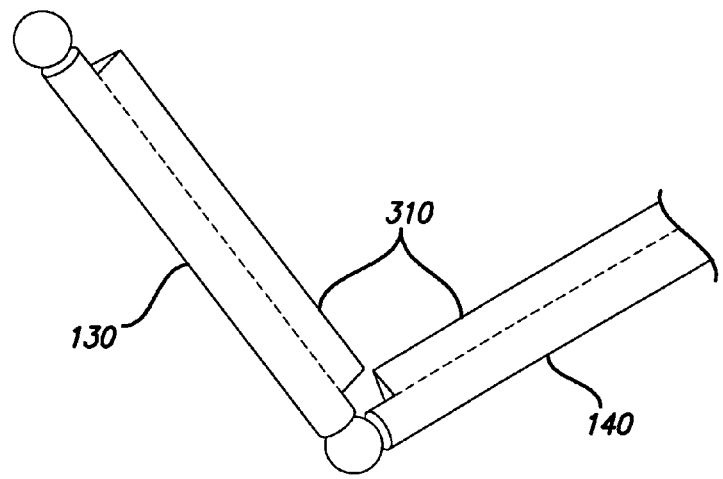

FIGS. 15A and 15B illustrate a longitudinal view of an umbrella stent, wherein portions of the proximal arms 130, distal arms 135 and outer struts 140 include a sharp edge 310.

The location of the sharp edges 310 may be selected based on the application for which the stent 100 is being employed. In one configuration, the sharp edges 310 may be located on the proximal arms 130, distal arms 135 and outer struts 140. In another configuration, the sharp edges 310 may be located solely on the outer struts 140. In a further configuration, the sharp edges 310 may be located on the proximal arms 130 and the distal arms 135.

When the sharp edge 310 is present on portions of the proximal arms 130, distal arms 135 and/or the outer struts 140, it is located on the interior of the proximal arms 130, distal arms 135 and/or the outer struts 140. Thus, when the sharp edge 310 is located on the outer struts 140, it is directed substantially toward the inner strut 105 and away from the tissue of the lumen in which the stent 100 is deployed. When the sharp edge 310 is present on the proximal arms 130, the sharp edge 310 is directed substantially toward the distal arms 135. When the sharp edge 310 is present on the distal arms 135, the sharp edge 310 is directed substantially toward the proximal arms 130.

The sharp edges 310 are located on the interior of the proximal arms 130, distal arms 135 and/or the outer struts 140 so that the sharp edge 310 will not damage the lumen in which the stent is deployed, either during deployment or removal.

The sharp edge 310 may assist in removal of the stent 100 when endothialization of the stent 100 has occurred. For example, if a layer of tissue envelops the outer strut 140, the proximal arms 130 and/or the distal arms 135 it may be difficult to remove the stent 100. The sharp edge 310, however, may serve to cut through the tissue that has enveloped the proximal arms 130, the distal arms 135 and/or the outer struts 140, allowing the stent 100 to be removed.

In one configuration, the sharp edge 310 may cut through the enveloping tissue during the removal process For example, when the stent 100 has been captured by the manipulation forceps 220, the physician can move the stent 100 proximally and distally within the lumen, which may in turn allow the sharp edges 310 to cut through the enveloping tissue. The process of collapsing the stent 100 may also serve to facilitate cutting by the sharp edges 310 of any enveloping tissue.

Figure 16A:
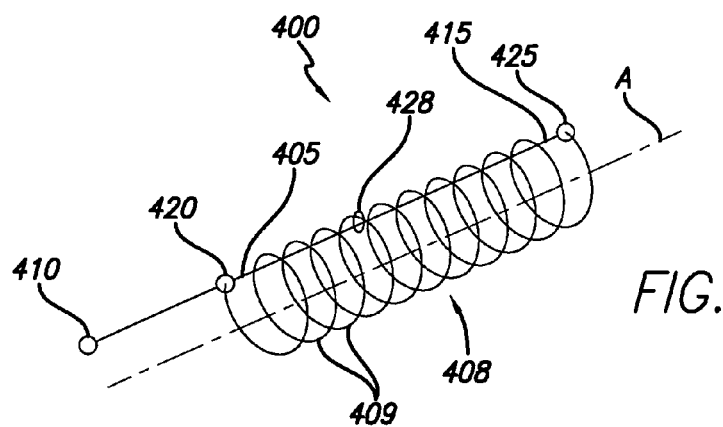
FIGS. 16A and 16B illustrate a longitudinal view of an alternative embodiment of a stent in a radially compressed state and a radially expanded state, respectively.
Figure 16B:
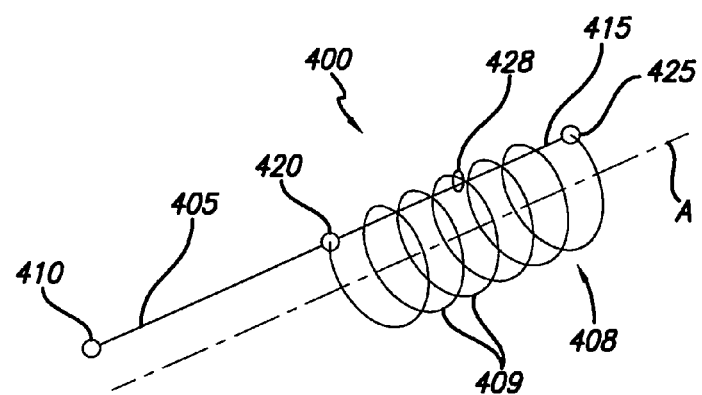

FIGS. 16A and 16B illustrate an alternative configuration for a stent 400 wherein the stent 400 includes a movable member 408 having a generally cylindrical shape. The stent 400 includes an inner strut 405 that extends from an inner strut proximal end portion 410 to an inner strut distal end portion 415 similar to the stent 100 described above. A first traveling anchor 420 may be movably attached to the inner strut 405 and a distal anchor 425 may be attached to the inner strut distal end portion 415. The traveling anchor 420 may be operably attached to the movable member 408. The movable member 408 may also be attached to the distal anchor 425. Attachment of the movable member 408 to the traveling anchor 420 and distal anchor 425 may be by any method known to one skilled in the art, for example as described above in relation to the stent 100. As shown in FIGS. 16A and 16B, the movable member 408 is in the shape of a helical coil having a lengthwise axis A and a radially compressed configuration when the traveling anchor 420 is in a first position in relation to the distal anchor 425 (FIG. 16A) and a radially expanded configuration when the traveling anchor 420 is in a second position in relation to the distal anchor 425 (FIG. 16B). As the traveling anchor 420 is moved toward the distal anchor 425, the movable member 408 radially expands, for example, by expanding loops 409, until the movable member is sized for an intraluminal delivery site. The traveling anchor 420 may also be moved away from the distal anchor 425, radially compressing the loops 409 of the movable member 408, for example, for delivery of the stent 400 to a body lumen or for removal of the stent 400 from a body lumen. The traveling anchor 420 may be positioned anywhere along the inner strut to provide the proper diameter stent 400 for delivery, removal, or any size delivery site. The distal anchor 425 may also be movable along the inner strut 405 and the relative positions of the traveling anchor 420 and the distal anchor 425 may determine the extent of radial expansion in the expanded configuration and the compressed configuration.

In some embodiments, the stent 400 may include one or more connectors 428 for slidably connecting a portion of the movable member 408 to the inner strut 405. The connector 428 may be used to position the strut 405 asymmetrically within the cylindrically shaped movable member 408, i.e., away from a central axis A extending though the cylindrical member 408. The connector may be sized and shaped to allow the loops 409 to expand radially outward as the traveling anchor 420 toward the distal anchor 425 and the compress radially inward as the traveling anchor 420 moves away from the distal anchor 425. For example, the connector 428 may be a ring that loosely circles the movable member 408 and the inner strut 405 to allow for movement of the movable member 408 and the inner strut 405 with respect to each other.

The stent 400 is similar to the stent 100 described above with the exception to the movable member 408. Other features of the stent 400, including, but not limited to the materials used to form the stent 400, features of the traveling anchor, the delivery and removal procedures, and the like are similar to the features described for the stent 100. Additional configurations for the movable member 408 are possible. By way of non-limiting example, the movable member may be formed in a generally cylindrical shape from a serpentine, coil, zigzag, flattened ribbon or any type pattern that forms a radially expandable and compressible movable member. In some embodiments, multiple movable members connected to the distal anchor 425 and one or more movable members 420 that cooperatively expand and compress may be used to form the stent 400.

Figure 17A:
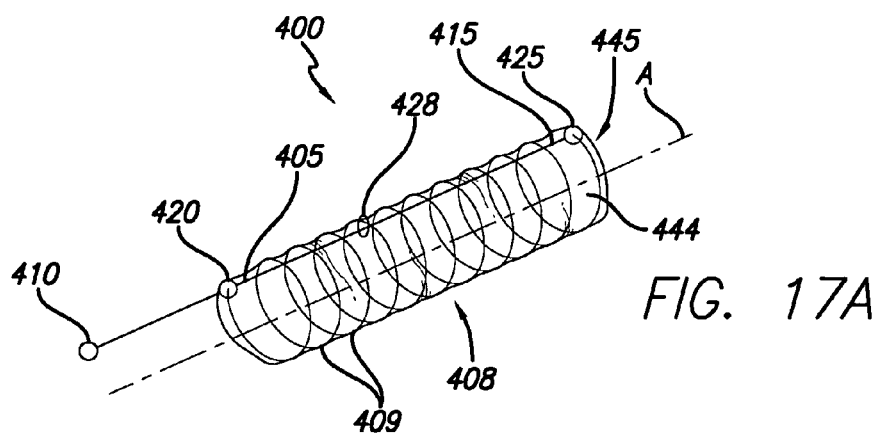
FIGS. 17A and 17B illustrate a longitudinal view of the embodiment shown in FIGS. 16A and 16B and having a cylindrical sleeve.
Figure 17B:
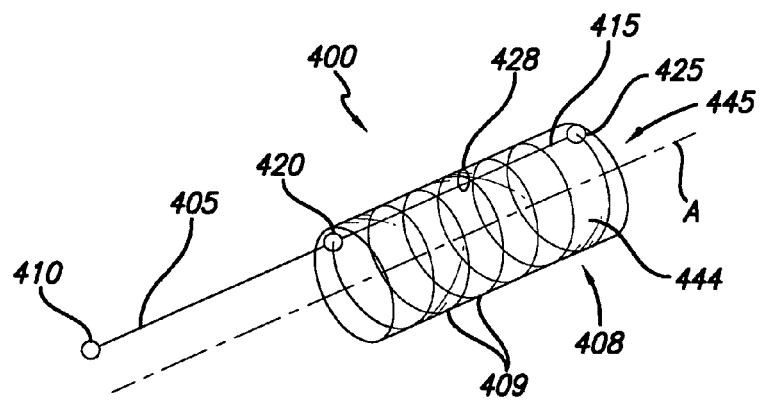

FIGS. 17A and 17B show illustrate the stent 400 shown in FIGS. 16A and 16B having a cylindrical sleeve 444 extending over the movable member 408. The sleeve 444 may extend over the entire movable member 408 or a portion of the movable member 408. The sleeve 444 defines a stent lumen 445. Similar to the sleeve 144, the sleeve 444 is adapted to collapse and expand with the movable member 408 and may be attached to the movable member 408 by any method known to one skilled in the art. The sleeve 444 may be made of similar materials as described above for the sleeve 144 wherein the material(s) used are flexible and capable of folding or collapsing in the collapsed configuration and expandable to cover the movable member 408 in the expanded configuration. In some embodiments, the sleeve 444 may be sized to tightly extend over the movable member 408 to help prevent ingrowth of a stricture or a tumor into the stent lumen 445.

The stent 100, 400 may be secured at the delivery site by radially expanding the stent 100, 400 and/or by physically or chemically adhering the stent 100, 400 to the delivery site. In some embodiments, the stent 100, 400 is removably secured to the delivery site. Exemplary techniques for attachment include physical adaptations such as barbs or hooks, suturing, stapling, bonding, gluing or otherwise adhering the valve 10 to the vessel wall 21 or combinations thereof. For example, the valve 10 may be secured in place with a tissue adhesive between the valve 10 and the vessel wall 21. Examples of tissue adhesives include, but are not limited to, fibrin glues, TISSEEL®, FLOSEAL®, BIOGLUE®, THOREX®, polyethylene glycol, and bovine or human derived thrombin, fibrinogen, and collagen. The attachment portion 46 may be secured to the vessel 21 with bioresorbable sealants and adhesives. Examples of bioresorbable sealants and adhesives include FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers- Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABONDTM, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

It is therefore intended that the foregoing detailed description be regarded as illustrative rather than limiting, and that it be understood that it is the following claims, including all equivalents, that are intended to define the spirit and scope of this invention.

The invention claimed is:

1. An expandable and retrievable stent comprising:
   an inner strut with an inner strut proximal end portion and an inner strut distal end portion;
   a distal anchor secured to the inner strut distal end portion;
   a plurality of distal arms operably attached to the distal anchor;
   a first traveling anchor movably attached to the inner strut, wherein the first traveling anchor is located between the inner strut proximal end portion and the inner strut distal end portion;
   a plurality of proximal arms operably attached to the traveling anchor; and a plurality of outer struts, wherein each outer strut extends between and is operably attached to one proximal arm at a proximal attachment and one distal arm at a distal attachment;

wherein said stent has three configurations, namely:

a first compressed state, wherein the distal arms are pivoted distally away from the distal anchor, the proximal arms are pivoted distally away from the traveling anchor and the traveling anchor is in a first position;

an expanded state, wherein the distal arms and the proximal arms are substantially perpendicular to the inner strut and the traveling anchor is in a second position; and a second compressed state, wherein the distal arms are pivoted proximally away from the distal anchor, the proximal arms are pivoted proximally away from the traveling anchor and the traveling anchor is in a third position; wherein the second position is between the first position and the third position; and wherein at least one of the distal anchor and the first traveling anchor is disposed on the inner strut within an area surrounded by the outer struts when said stent is in the first compressed state and outside the area surrounded by the outer struts when said stent is in the second compressed state.

2. The expandable and retrievable stent of claim 1, further comprising:

a second traveling anchor, wherein the second traveling anchor is distal to the first traveling anchor and proximal to the distal anchor; and a plurality of central arms operably attached to the second traveling anchor, wherein each central arm is operably attached to one of the outer struts.

3. The expandable and retrievable stent of claim 1, further comprising a cylindrical sleeve, wherein the cylindrical sleeve is attached to the plurality of outer struts.

4. The expandable and retrievable stent of claim 3, wherein the cylindrical sleeve includes at least one biologically active compound.

5. The expandable and retrievable stent of claim 1 wherein the proximal arms and the distal arms are attached to the first traveling anchor, the distal anchor and the outer struts by way of eyelets.

6. The expandable and retrievable stent of claim 1, wherein a surface of the inner strut comprises sloping teeth and the first traveling anchor comprises a pawl.

7. The expandable and retrievable stent of claim 1 wherein the outer struts are convex.

8. The expandable and retrievable stent of claim 1, wherein the traveling anchor is convertible from a reduced diameter to an expanded diameter.

9. The expandable and retrievable stent of claim 1, wherein the surface of the inner strut comprises spiral threads and the traveling anchor comprises grooves corresponding to the spiral threads.

10. The expandable and retrievable stent of claim 1, wherein the stent comprises a bioabsorbable material.

11. The expandable and retrievable scent of claim 1, wherein the stent or selected portions of the stent comprise a coating.

12. The expandable and retrievable stent of claim 11, wherein the coating comprises at least one biocompatible polymeric material.

13. The expandable and retrievable stent of claim 11, wherein the coating comprises at least one biologically active material.

* * * * *

UNITED STATES PATENT AND TRADEMARK OFFICE
CERTIFICATE OF CORRECTION

PATENT NO.       : 7,727,270 B2                                                Page 1 of 1
APPLICATION NO.  : 11/414977
DATED            : June 1, 2010
INVENTOR(S)      : Brian K. Rucker It is certified that error appears in the above-identified patent and that said Letters Patent is hereby corrected as shown below:

On Title page, Item (73) the name of assignee is not listed; assignee should be listed as --Wilson-Cook Medical Incorporated, Winston-Salem, NC (US)--

On Title page, Item (74) the name of the Attorney, Agent, or Firm is not listed; Attorney, Agent, or Firm should be listed as --Buchanan Intellectual Property Office LLC--

Signed and Sealed this

Ninth Day of November, 2010

David J. Kappos
*Director of the United States Patent and Trademark Office*